(12) United States Patent
Engheta et al.

(10) Patent No.: US 7,489,391 B2
(45) Date of Patent: Feb. 10, 2009

(54) POLARIZATION AND REFLECTION BASED NON-CONTACT LATENT FINGERPRINT IMAGING AND LIFTING

(75) Inventors: Nader Engheta, Berwyn, PA (US); Edward N. Pugh, Jr., Philadelphia, PA (US); Shih-Schon Lin, Philadelphia, PA (US); Konstantin Marianovich Yemelyanov, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/587,349

(22) PCT Filed: Apr. 27, 2005

(86) PCT No.: PCT/US2005/014547

§ 371 (c)(1),
(2), (4) Date: Jul. 5, 2007

(87) PCT Pub. No.: WO2006/073450

PCT Pub. Date: Jul. 13, 2006

(65) Prior Publication Data

US 2007/0280513 A1    Dec. 6, 2007

Related U.S. Application Data

(60) Provisional application No. 60/565,669, filed on Apr. 27, 2004.

(51) Int. Cl.
*G06K 9/74* (2006.01)
(52) U.S. Cl. ........................................................ 356/71
(58) Field of Classification Search ................... None
See application file for complete search history.

(56) References Cited

U.S. PATENT DOCUMENTS

2002/0087085 A1 *   7/2002   Dauga ........................ 600/476

FOREIGN PATENT DOCUMENTS

WO    WO2006/073450 A2    7/2006

OTHER PUBLICATIONS

Cook, R.L., et al., "A reflectance model for computer graphics," Computer Graphics, 1981, 15(3), 307-316.
Dalrymple, B.E., et al., "Inherent fingerprint luminescence-detection by laser," J. Forensic Science, 1977, 22(1), 106-115.
Dalrymple, B.E., et al., "Computer enhancement of evidence through background noise suppression," J. Forensic Sci., 1994, 39(2), 537-546.
Demos, S.G., et al., "Optical fingerprinting using polarization contrast improvement," Electronics Letters, 1997, 33(7), 582-584.
Kaymaz, E., et al., "A novel approach to fourier spectral enhancement of laser-luminescent fingerprint images," J. Forensic Science, 1993, 38(3), 530-541.
Ko, T., "Fingerprint enhancement by spectral analysis techniques," IEEE, Proc. Of the 31st Applied Imagery Pattern Recognition Workshop, 2002, 133-139.
Nayar,S.K., et al., "Surface reflection: physical and geometrical perspectives," IEEE Transactions on Pattern Analysis and Machine Intelligence, 1991, 13(7), 611-634.
Neate, E., Personal Website of Esther Neate, a crime lab specialist, "History of fingerprint identification," 2 pages, http://www.eneate.freeserv.co.uk/page5.html, downloaded from the internet on Jul. 23, 2007; "Digital fingerprints," 1 page, http://www.eneate.freeserve.co.uk/page24.html, downloaded from the internet on Jul. 23, 2007.
Neate, Personal Website of Esther Neate, a crime lab specialist, "A digital solution," http://www.eneate.freeserve.co.uk/digital__.PDF; 2003, 1-6.
Phong, B.-T., "Illumination for computer generated pictures," Communications of the ACM, 1975, 18(6), 311-317.
Schwind, R., "Zonation of the optical environment and zonation in the rhabdom structure within the eye of the backswimmer, *Notonecta glauca*," Cell Tissue Res., 1983, 232, 53-63.
Schwind, R., The plunge reaction of the backswimmer *Notonecta glauca*, J. of Comparative Physiology A, 1984, 155, 319-321.
Torrance, K.E., et al., "Theory of off-specular reflection from roughened surfaces," J. Opt. Soc. Am., 1967, 57(9), 1105-1114.
Wehner, R., "Matched filters'-neural models of the external world," J. of Comparative Physiology A, 1987, 161, 511-531.
Wolff, L.B., "Relative brightness of specular and diffuse reflection," Optical Engineering, 1994, 33(1), 285-292.
Wolff, L.B., "Polarization camera sensors," Image and Vision Computing, 1995, 13(6), 497-510.

\* cited by examiner

*Primary Examiner*—Michael P Stafira
(74) *Attorney, Agent, or Firm*—Woodcock Washburn, LLP

(57) ABSTRACT

An optical fingerprinting method extracts high quality latent fingerprints from a surface without any invasive chemical or physical contact with the examined object, and requires no cooperation of the subject. Rather than employing extraneous material, the optical properties of the latent fingerprint are used to generate one or more images with sufficient contrast to distinguish the latent fingerprint or some other deformation in the surface. The system includes a light source oriented to apply light at an angle of incidence to the surface at the position to be examined for the latent fingerprint or deformation, a camera oriented to receive light specularly and diffusely reflected from the surface and/or by the fingerprint or deformation on the surface, and a processor that performs the computation for digital contrast enhancement and/or reprojection of the recovered fingerprint image to a frontal view if necessary. The technique uses optical polarization properties to enhance the images by placing a linearly polarized filter(s) in front of the observing camera. At least two pictures of the same scene with the same lighting and view angle arrangement are taken whereby each of the pictures differ only in that the orientations of the polarization filter are different. At least two light polarization parameters for each pixel are computed from the two or more images taken with different polarizer orientations. An image with each pixel value representing the value of one of the polarization parameters or a function of the polarization parameters is generated and displayed, with some digital contrast enhancement and/or reprojection applied. The hidden latent fingerprint pattern is revealed in at least one such image with the interfering background pattern significantly suppressed.

17 Claims, 15 Drawing Sheets

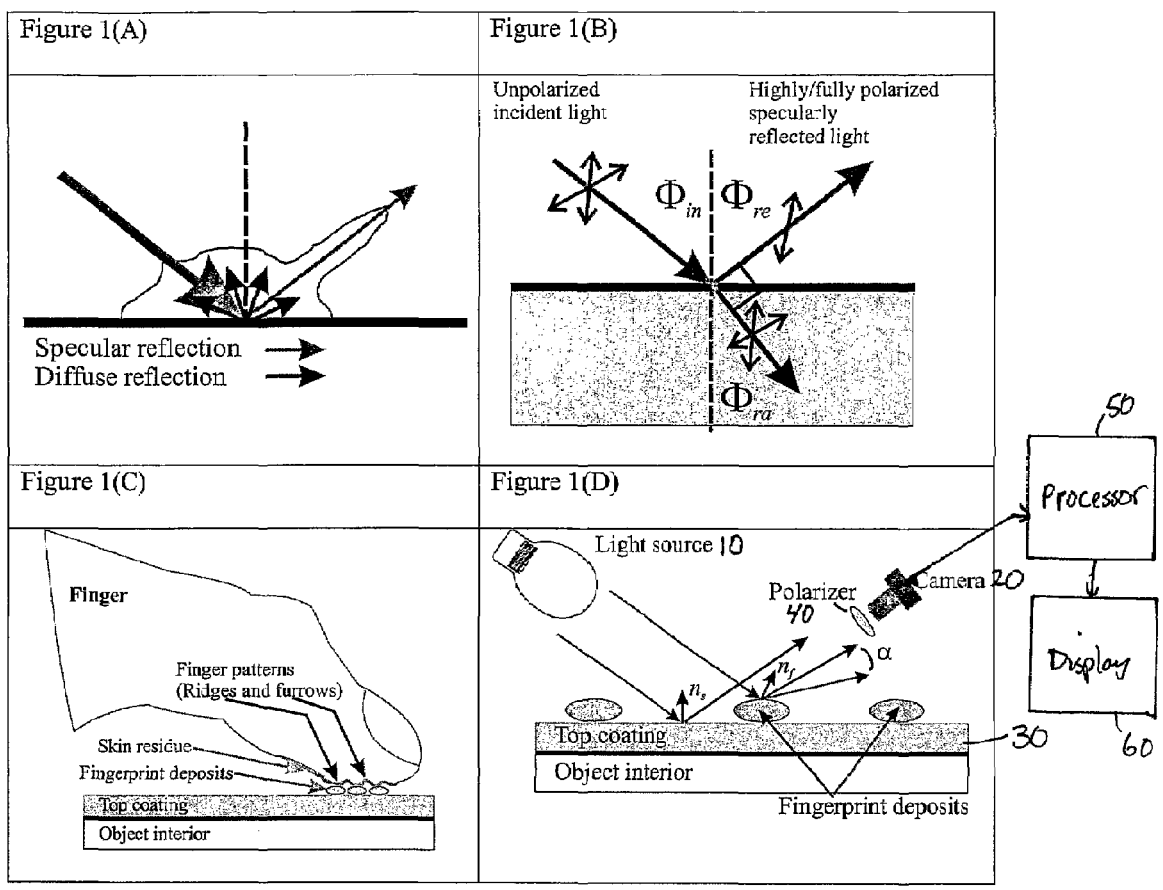

POLARIZATION AND REFLECTION BASED NON-CONTACT LATENT FINGERPRINT IMAGING AND LIFTING

CROSS-REFERENCE TO RELATED APPLICATIONS

This application is the National Stage of International Application No. PCT/US2005/014547, filed Apr. 27, 2005, which claims the benefit of the filing date of U.S. Provisional Application No. 60/565,669, filed Apr. 27, 2004, the disclosure of which is incorporated herein by reference in its entirety.

GOVERNMENT INTEREST

The present invention was supported in part by the U.S. Air Force Office of Scientific Research (AFOSR), through grants F49620-01-1-0470, F49620-02-1-0140, and the DURIP grant F49620-02-1-0241. The government may have certain rights in the invention.

FIELD OF THE INVENTION

The present invention relates to a method and apparatus for imaging and lifting fingerprints and, more particularly, to a method and apparatus for non-contact latent fingerprint imaging and lifting based on polarization and reflection differences in the visible band found between latent fingerprint marks and the underlying surfaces.

BACKGROUND OF THE INVENTION

Fingerprinting is one of the most widely used biometric methods for identifying and authenticating individual persons. The modem science of fingerprinting started in the second half of the $19^{th}$ century. There are two types of fingerprint data, distinguished by their formation processes. In forensic science, finger marks left unintentionally by a suspect at a crime scene are referred to as "latent fingerprints," while fingerprints acquired directly from human fingers using ink or scanners in controlled environments are referred to as "exemplar fingerprints." Latent fingerprints differ from exemplar fingerprints in that they are very difficult to detect with unaided human vision under most ordinary viewing conditions (hence their names). Latent fingerprints are usually of lower quality, although it is sometimes possible to find high quality fingerprint marks at a crime scene. These latter fingerprints are called "patent fingerprints." Nonetheless, it is the latent fingerprints that are more common and require greater efforts to render visible. Most techniques employed for this purpose utilize a chemical or physical process that applies some kind of material directly to the surface suspected to bear fingerprints. Once the contrast of the fingerprint mark is sufficiently enhanced by such treatments, the mark is either photographed or "lifted" in order to be permanently archived as evidence. The term "lifting the fingerprint" originates from the oldest, but still widely used fingerprint detection method—powdering—in which the powders applied adhere to the fingerprint material, and then are physically lifted out of the original crime scene object by a sticky tape.

The currently popular latent fingerprint detection and extraction methods used by law enforcement agencies include, but are not limited to, powdering, iodine fuming, ninhydrin and DFO application, silver nitrate development, cyanoacrylate (glue) fuming, gentian violet staining, episcopic coaxial illumination, laser excited luminescence, and RUVIS (Reflected Ultra Violet Imaging System). Despite these options, there is still a need for new methods because every existing method tends to be unsuitable for some surfaces, due either to its inadequacy in lifting the print from, or to its damaging side effects to the surfaces. In particular, the chemical and physical processing involved to extract latent fingerprints can inflict deleterious effects upon the objects being examined. Thus, often valuable and irreplaceable objects cannot be searched for fingerprints at all. Furthermore, the chemicals used to enhance fingerprint contrast or to induce luminescence may need long processing time, are often toxic, environmentally unfriendly, or even radioactive. Several ingredients used in dusting powders are also known to be toxic or posing potential health hazards, e.g. titanium oxide and manganese dioxide. They can be harmful to the operator if not handled correctly because they are designed to react with or adhere to the fingerprint residues, which are the same material found on human skin. Some chemicals require specific solvents that have undesirable side effects (e.g., methanol (in DFO solution) and phenol (in Gentian violet solution) are poisonous); indeed, some solvents used for fingerprint enhancement have actually been banned because of their damage to the environment, e.g. solvent HFE7100.

There have been a two attempts to develop non-contact latent fingerprint detection and lifting methods, but so far each of them has had its specific shortcomings. The episcopic coaxial illumination method uses a semitransparent mirror to project the light source at a right angle to the surface and to observe the surface also from the right angle. However, this arrangement cannot allow adjustment in lighting angle and observation angles, and both are known to greatly affect the resulting contrast of fingerprint patterns. In addition, the reflection seen at a right angle does not show polarization contrast which the method of the present invention utilizes to further enhance the visibility of latent fingerprints.

Lasers have provided an optical method for lifting latent prints, utilizing induced luminescence of the fingerprint material. However, there are limitations to this method as well. In its original non-contact form the natural fluorescence signal is often very weak, thus requiring a very powerful laser at blue/green wavelength. These powerful lasers are very expensive and generally not portable due to bulky size of the power and cooling requirements. More portable lasers and arc lamps have been found useful to substitute for the fluorescence light source only when used with chemical florescence enhancers (and are thus invasive). Also, the laser must operate in the near ultraviolet and have adequate rating. Such laser equipment is fairly expensive and requires trained technicians to be operated safely. The fact that all organic substances can fluoresce when excited by a laser also causes significant background noise. In addition, many commonly found surfaces, e.g. several kinds of paper, will fluoresce even stronger than the fingerprint residue when illuminated by laser. Thus, laser-excited luminescence, like other existing methods, can not be applied to certain types of surfaces and are most often used with the aid of applying fluorescence enhancing chemicals, the use of which negates the non-contact advantage.

RUVIS is another non-contact method that takes advantage of the contrast differences between the fingerprint and the underlying surface. The equipment used is more portable and less expensive than the powerful laser required in the non-contact laser fluorescence method, but the RUVIS equipment is still much more expensive than the ordinary visible band optical equipment used to implement the method of the invention. This method is successful in some cases but not in some other cases. It is found again that pretreatment with fluorescence enhancing chemicals produces better results in many cases. Thus, RUVIS may be more practical when used as an invasive method.

Automated optical fingerprint extraction systems are commercially available. One proposed system utilizes laser light with a polarizer to extract fingerprint images directly from the live human finger. However, most of such systems are designed to take exemplar fingerprints, i.e. from subjects who cooperate with the system during the acquisition of fingerprint images. As explained above, exemplar fingerprint extraction is a very different application field than latent fingerprint extraction. Exemplar fingerprint scanning systems are used primarily for security systems or law enforcement facilities where the users cooperate with the fingerprint extraction devices but would be totally useless for extracting latent fingerprints at a crime scene.

An optical fingerprinting method is desired that extracts high quality latent fingerprints without any invasive chemical or physical contact with the examined object, and requires no cooperation of the subject. Rather than employing extraneous material, a method is needed that takes advantage of the optical properties of the latent fingerprint, which include sweat (salty water), grease, and lipid, all of which are rather transparent dielectric materials, making them difficult to detect under most viewing conditions. The present invention satisfies these needs in the art.

SUMMARY OF THE INVENTION

A well known "trick of the trade" in the law enforcement community is to shine a flashlight on surfaces to reveal the general location of otherwise hard-to-detect latent fingerprints. As noted above, the common practice is then to apply powdering or staining enhancement, and finally a lifting or a photograph is taken of the physically enhanced fingerprint. Interestingly, it seems that the use of such lighting has not been regarded as a sufficient enhancement method on its own, partially due to the lack of readily available image processing hardware and software only a few years ago. The present invention provides a scientific explanation of this trick of the trade and at the same time expands the detection capability several fold with the use of more elaborate theory and equipment.

The present invention also addresses the above-mentioned needs in the art by providing a completely non-invasive method that recovers latent fingerprint images or other deformations on a surface based on optical polarization and specular reflection phenomena in the visible regime, and which yields results of comparable or better quality to those of existing, mostly invasive, methods. In particular, an exemplary embodiment of a method of generating an image of a deformation such as a latent fingerprint on a surface in accordance with the invention comprises the steps of:

applying light to the surface at a position to be examined for the deformation, the light having an angle of incidence with the surface in such a way that the specularly reflected component of the light from the light source by the surface and/or by the deformation will be captured by an observing camera;

receiving light specularly and diffusely reflected from the surface and/or by a deformation on the surface in the observing camera after the light at the angle of incidence has interacted with the surface and the deformation;

generating two or more images of the specularly and diffusely reflected light received by the camera from the surface;

processing the two or more images to extract polarization parameters including light intensity and/or light polarization; and displaying an image of the deformation, where the image pixel values comprise light intensity and/or light polarization of the reflected light from the surface at the position.

In an exemplary embodiment, a polarizer is added between the observed surface and the camera. The method of the invention further includes the steps of orienting the polarizer at two or more different angles when generating the two or more images, extracting fundamental polarization light intensity ($I_U$), polarized light intensity difference ($I_A$), and/or angle of the major axis of the polarization ellipse ($\theta$) during the processing step, and displaying an image of $I_U$, $I_A$, $\theta$, $I_A/I_U$ or a digitally contrast enhanced version of these images. The latent fingerprint images tend to appear greatly enhanced in contrast in at least one of these images while the unrelated background patterns are greatly suppressed at the same time.

The system for implementing such a method in accordance with the invention includes a light source oriented to apply light at an angle of incidence to the surface at the position to be examined for the deformation and a camera oriented to receive light specularly and diffusely reflected from the surface and light diffusely reflected by a deformation on the surface, with/without a polarizing filter. When the polarization processing is desired for a particular surface, the polarization filter is used in order to capture the polarization data at different polarizations in respective images. A processor is also provided that generates two or more images of the specularly and diffusely reflected light received by the camera, processes the two or more images to extract at least two polarization parameters including polarization light intensity ($I_U$), polarized light intensity difference ($I_A$), and/or angle of the major axis of the polarization ellipse ($\theta$), and provides a digital contrast enhancement like linear rescale or histogram equalization if needed. The digital contrast enhancement is only done to adjust to the intensity sensitivity of the human viewers. The critical enhancement of the fingerprint pattern and the suppression of the background pattern are the results of the imaging method of the invention. Simply applying the digital contrast enhancement method to a picture of the surface taken by an ordinary camera without using the arrangement and procedure of the invention would not reveal the hidden latent fingerprint pattern nor suppress the unwanted background pattern. In accordance with the invention, each pixel of the resulting image can represent the light intensity and/or the value of certain light polarization parameters of the reflected light from the surface at the position. In an exemplary embodiment of the invention, different polarization filters are provided that are respectively disposed between the surface and the camera when respective images of the two or more images are generated. For example, the polarization filters may have angles of 0°, 45° and 90°, although other polarization filter angles may of course be used.

The processor includes software that processes the images to improve intensity contrast and/or polarization contrast between a portion of the image containing the surface and a portion of the image containing the deformation. The processor may be further programmed to present to a display for selection by a user calculated light intensity information at each pixel of the image, calculated light polarization information at each pixel of the image, and a combination image where each pixel comprises a function (e.g., product) of the calculated light intensity information and the calculated light polarization information. On the other hand, the processor may be programmed to automatically display the light intensity image, the image containing the light polarization information, and/or the combination image based on reflection characteristics of the surface.

These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which:

FIG. 1(A) illustrates that macroscopic reflection from a surface consists of two distinct kinds, i.e. specular and diffuse.

FIG. 1(B) illustrates partial polarization of specularly reflected light from a semi-transparent dielectric surface.

FIG. 1(C) illustrates a cross-section view of a fingerprint on a surface showing how the ridge area of the skin pattern on a finger tends to leave a dielectric residue on a surface touched by the finger so as to form a latent fingerprint.

FIG. 1(D) illustrates an exemplary embodiment of the physical apparatus used to implement the methods of the invention.

FIG. 2(A) illustrates an ordinary picture taken without the setup of the invention showing no fingerprint even after digital contrast enhancement; FIG. 2(B) illustrates a picture taken with the setup of the invention with the surface reflecting specularly while the fingerprint pattern reflects only diffusely so as to reveal the hidden latent fingerprint pattern; and FIG. 2(C) illustrates the image of the polarization parameter $I_A$ after polarization imaging and processing so as to reveal an enhanced fingerprint pattern and a greatly suppressed unrelated background pattern.

FIG. 3(A) illustrates an ordinary picture taken without the setup of the invention showing no fingerprint even after digital contrast enhancement; FIG. 3(B) illustrates a picture taken with the setup of the invention with the surface reflecting specularly while the fingerprint pattern reflects only diffusely so as to reveal the hidden latent fingerprint pattern; and FIG. 3(C) illustrates the image of the polarization parameter $I_A$ after polarization imaging and processing so as to reveal an enhanced fingerprint pattern and a greatly suppressed unrelated background pattern.

FIG. 4(A) illustrates an ordinary picture taken without the setup of the invention showing no fingerprint even after digital contrast enhancement; FIG. 4(B) illustrates a picture taken with the setup of the invention with the surface reflecting specularly while the fingerprint pattern reflects only diffusely so as to reveal the hidden latent fingerprint pattern; and FIG. 4(C) illustrates the image of the polarization parameter $I_A$ after polarization imaging and processing so as to reveal an enhanced fingerprint pattern and a greatly suppressed unrelated background pattern.

FIG. 5(A) illustrates an ordinary picture taken without the setup of the invention showing no fingerprint; FIG. 5(B) illustrates a digital contrast enhancement of FIG. 5(A) showing that the fingerprint is still invisible; FIG. 5(C) is a picture taken with the setup of the invention with the surface reflecting specularly while the fingerprint pattern reflects only diffusely so as to reveal the hidden latent fingerprint pattern; FIG. 5(D) illustrates a digital contrast enhancement of FIG. 5(C) showing that the detection is not the result of digital contrast enhancement; FIGS. 5(E) and 5(F) illustrate an enlarged zoom in view of FIG. 5(D) showing the quality of the recovered latent fingerprint image; and FIG. 5(G) illustrates a digitally "rectified" view of FIG. 5(D) showing that digital reprojection can easily correct the oblique view angle used in the original images.

FIG. 6(A) illustrates an image using specular reflection only where the background patterns are visible together with the fingerprint; FIG. 6(B) illustrates the polarization processing result of the polarized intensity where the background patterns are completely removed; and FIG. 6(C) illustrates a zoom-in view of FIG. 6(B).

FIG. 7(A) illustrates an ordinary picture taken without the lighting setup and polarizer of the invention whereby there is no visible fingerprint pattern; FIG. 7(B) illustrates a processed polarized component image showing the fingerprint pattern in high contrast; FIG. 7(C) illustrates a zoom-in view of FIG. 7(B); and FIG. 7(D) is a rectified view of FIG. 7(C).

DETAILED DESCRIPTION OF ILLUSTRATIVE EMBODIMENTS

Figure 2A:
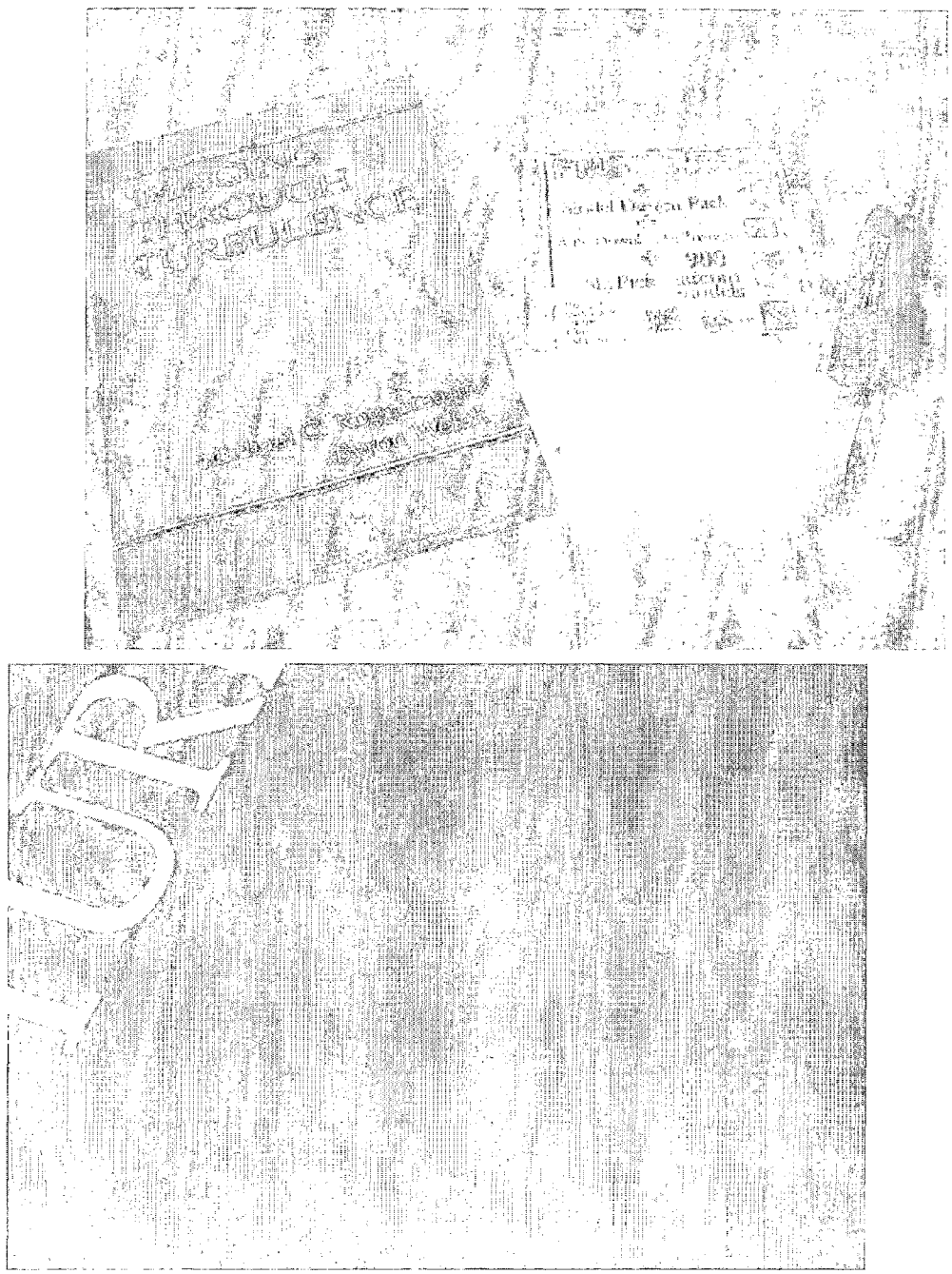
FIGS. 2(A)-2(C) illustrate the fingerprint detection and lifting capabilities of the invention applied to a hard cover book using the configuration of FIG. 1(D).

The invention will be described in detail below with reference to FIGS. 1-7. Those skilled in the art will appreciate that the description given herein with respect to those figures is for exemplary purposes only and is not intended in any way to limit the scope of the invention. All questions regarding the scope of the invention may be resolved by referring to the appended claims.

As will be described in detail below, the present invention relates to a new optical detection technology that allows detection and "lifting" of latent fingerprints into clearly identifiable digital images without the application of chemical treatments or any physical contact with the surface and fingerprint material. The resulting images have comparable or better quality to those obtained by conventional methods.

Exemplary Embodiment

FIG. 1 illustrates the physical principles concerning non-contact latent fingerprint detection and extraction in accordance with the invention. FIG. 1(A) illustrates that macroscopic reflection from a surface consists of two distinct kinds, i.e. specular and diffuse. For specular reflection, the angles of incidence and reflection are equal, while for the diffuse case the reflected intensity may have an effectively uniform distribution over all directions in a hemisphere. Most surfaces exhibit both types of reflections, but one type may be stronger than the other. In fact, in most cases, the specular reflection are usually 10-30 times stronger than the diffuse reflection component. FIG. 1(B) illustrates partial polarization of specularly reflected light from a semi-transparent dielectric surface. Since the Fresnel reflection coefficients for the parallel and perpendicular polarizations are generally different, the light reflected from the smooth surface is partially polarized with the polarization being perpendicular to the plane of incidence.

Live human skin is kept soft and pliable by the constant oily secretion of hypodermic glands. As illustrated in FIG. 1(C), the ridge area of the skin pattern tends to leave a dielectric residue on a surface touched by a finger. The residue left forms the latent fingerprint. This residue pattern is often hidden from normal viewers because the residue materials are mostly semitransparent in visible light so they tend to completely blend in with the background pattern or color of the surface. Most existing techniques to detect these hidden latent fingerprints apply chemicals or powders that adhere to or chemically react with the residue to produce a colored or fluorescent pattern. As will be explained in more detail below, the apparatus of FIG. 1(D) is used in accordance with the invention to detect and extract such latent fingerprints. In particular, the inventors show herein that by using a method that generates a sufficient contrast difference between the latent fingerprint and the rest of the surface in the camera image, a successful detection and extraction can be achieved without applying physical or chemical treatments to the surface. For example, the camera position in FIG. 1(D) is oriented in such a way that it captures the specular component of reflected light from the clean surface only while a substantial portion of the specular reflection component of the residue is not captured. Moreover, while the human eye tends to detect intensity and wavelength information but not polarization information in light, the polarization information may contain useful information for providing contrast differences desirable to detect latent fingerprints on certain surfaces. The present invention provides a mechanism for using the polarization information in light to detect variations in surfaces and to make those changes visible to the human eye.

As illustrated in FIG. 1(C), when a finger touches the object surface, a dielectric residue mark bearing the fingerprint pattern is imprinted on it. The residue on the surface induces differences in optical polarization or reflection or both between the clean part of the surface and that bearing the print. The optical information is captured and enhanced by the optical setup of FIG. 1(D) of the invention and stored in RAW digital images. Further digital processing of the captured images by a processor enables one to "develop" or "lift" the latent fingerprint pattern without applying any powder or other chemicals to the object. The optical setup of FIG. 1(D) is designed on the basis of Fresnel reflection theory for orthogonal polarizations and the theories for macroscopic surface reflectance developed for computer vision and graphics.

The inventors note that biologists and zoologists have found that certain animal species have visual systems that sense and utilize (in or near) visible light's polarization in the natural environment. For example, backswimmer *Notonecta glauca* can detect the polarization of light reflected from smooth water surfaces and use it to land and plunge safely on the water surface. The original step to design the optical setup for latent fingerprint detection was inspired from this ability of *Notonecta glauca* in detecting the surface of the water.

As shown in the cross section view of the fingerprint on a surface in FIG. 1C, the ridge area corresponds to a small amount of residue on the surface, while the furrow area does not. Most existing enhancement methods take advantage of this situation by applying materials that selectively attach to or interact with only the residue area and produce a colored or fluorescent pattern of the residue area. The non-contact method of the invention exploits this situation in a different way. As illustrated in FIG. 1(D), a common household light source 10 (incandescent or fluorescent, does not really matter here), a camera 20, and the surface 30 being inspected are arranged in such a way that the geometry conforms approximately to the law of (specular) reflection. Thus, the incident angle of light from the source 10 approximately equals the viewing (reflection) angle of the camera 20, so that the camera 20 will capture the light reflected specularly from the non-residue area, and also only the light reflected diffusely from the residue laden area. The reason is that the residue stain area is likely to have different surface normal directions as compared with the uniform or smoothly varying surface normal direction of the unstained surface area. The highly localized nature of specular reflection energy distribution makes it very sensitive to even minute changes in the direction of surface normal. Since the specular reflection component is, in general, much stronger than the diffuse reflection component (FIG. 1(A)), one potentially finds an enhanced contrast between the residue laden ridge mark and the clean surface furrow 'negative-mark'. Depending on the surface pattern and color, sometimes it will be beneficial to adjust for the camera 20 and the lighting so that only the specular component of the residue is captured and a 'positive mark' is seen.

Sometimes this contrast enhancement from the specular reflection effect alone is insufficient. The object itself may have a complicated high contrast pattern under the top coating of the surface 30 that interferes with the fingerprint pattern even after the enhancement. This problem has been recognized by those skilled in the fingerprinting art. An additional characteristic of the specular reflection is that it tends to be partially polarized in a plane perpendicular to the plane of reflection, as shown in FIG. 1(B). Thus, one or more polarization analyzers collecting polarization components at different angles can be used to provide complete information about the polarization state of the reflected light. For this purpose, a polarization filter or analyzer 40 may be placed over the lens of the detection camera 20. Based on the polarization information received through the polarization filter or analyzer 40, one can further extract only the specular component of this reflection and get a much cleaner fingerprint image, since for the most part the light coming from the pattern beneath the top coating of the object surface 30 is due mostly to unpolarized, diffuse reflection.

Once the polarization state of the reflected light has been obtained by the camera 20, a processor 50 may perform the calculations set forth below to determine at least two polarization parameters for each pixel in the image from parameters including a total pixel intensity (referred to in the equations below as double the value of '$I_U$'), a degree of linear polarized pixel intensity (or polarization difference intensity) at a pixel (referred to in the equations below as '$I_A$'), and an orientation angle of a major axis of a polarization ellipse (referred to in the equations below as '$\theta$'). Once calculated, an image of the light intensity information at each pixel, an image of the light polarization information at each pixel, and/or an image where each pixel is a function (e.g., a product) of the light intensity and light polarization at each pixel can be formed such that each pixel in the image represents the relative value of one of the polarization parameters or other calculated quantities instead of the regular light intensity as in normal pictures. Each of these images may be selectively displayed on display 60 and contrast enhanced so that the viewer may select for display the image providing the best contrast between the surface 30 and the fingerprint. On the other hand, the image displayed may be predetermined based on the reflection characteristics of the surface 30 the latent fingerprint is on (e.g., highly reflective surfaces might achieve sufficient contrast with the intensity image, while highly diffusive surfaces might achieve better contrast with the polarization image.

Figure 2B:
Figure 2C:
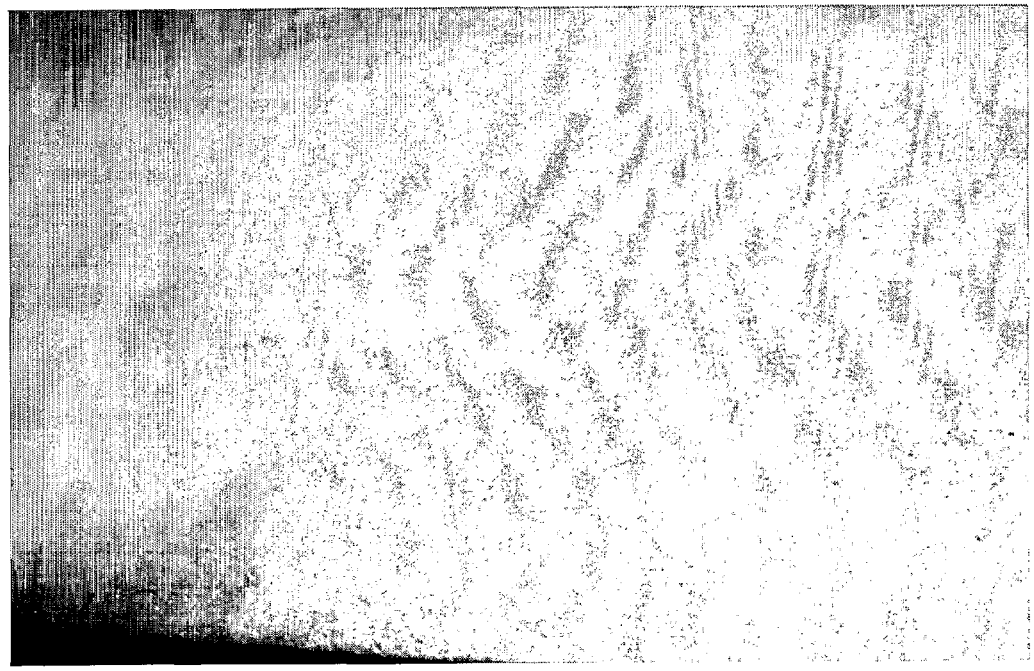
Figure 3A:
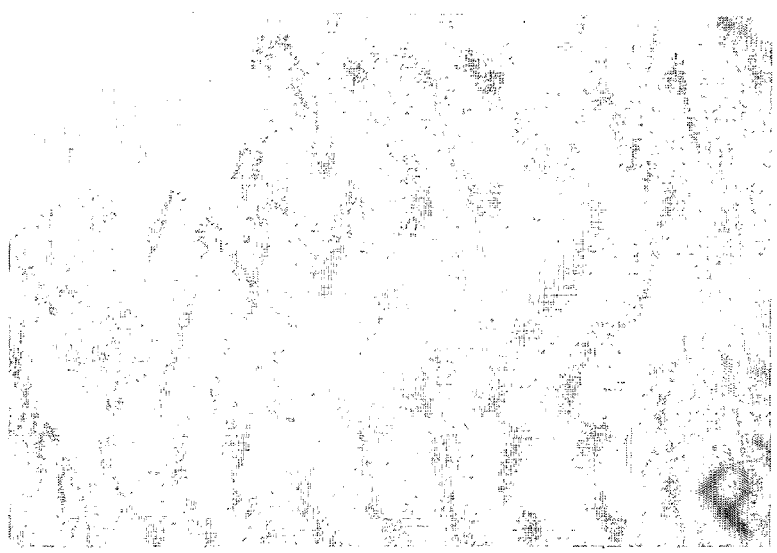
FIGS. 3(A)-3(C) illustrate the fingerprint detection and lifting capabilities of the invention applied to a plastic CD case using the configuration of FIG. 1(D).
Figure 3B:
Figure 3C:
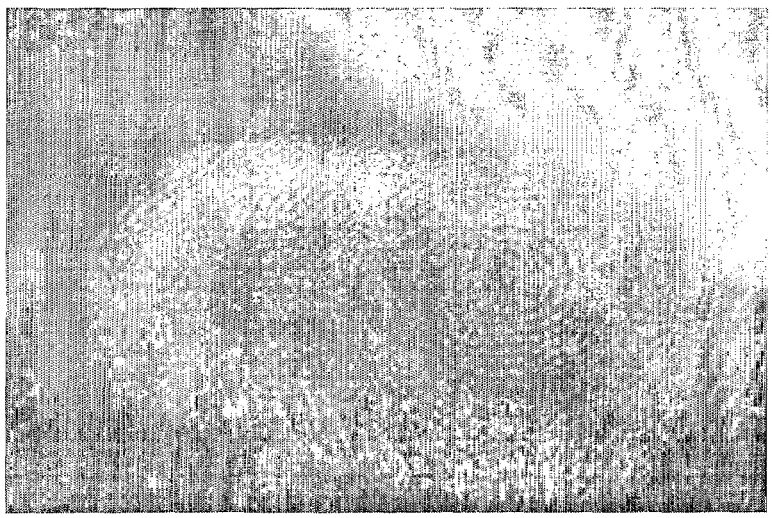
Figure 4A:
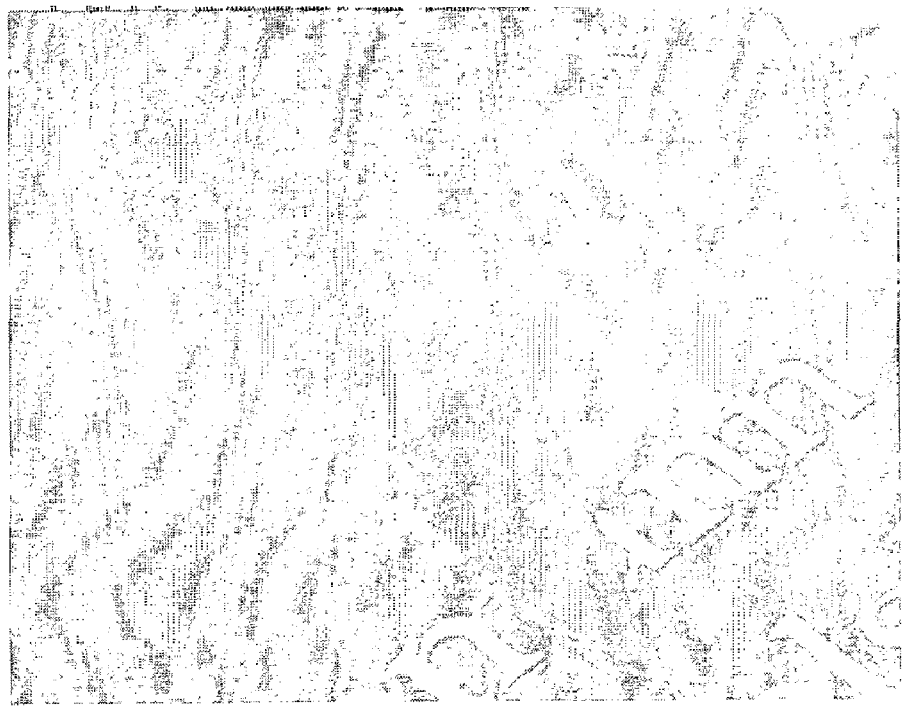
FIGS. 4(A)-4(C) illustrate the fingerprint detection and lifting capabilities of the invention applied to a steel Swiss army knife using the configuration of FIG. 1(D).
Figure 4B:
Figure 4C:
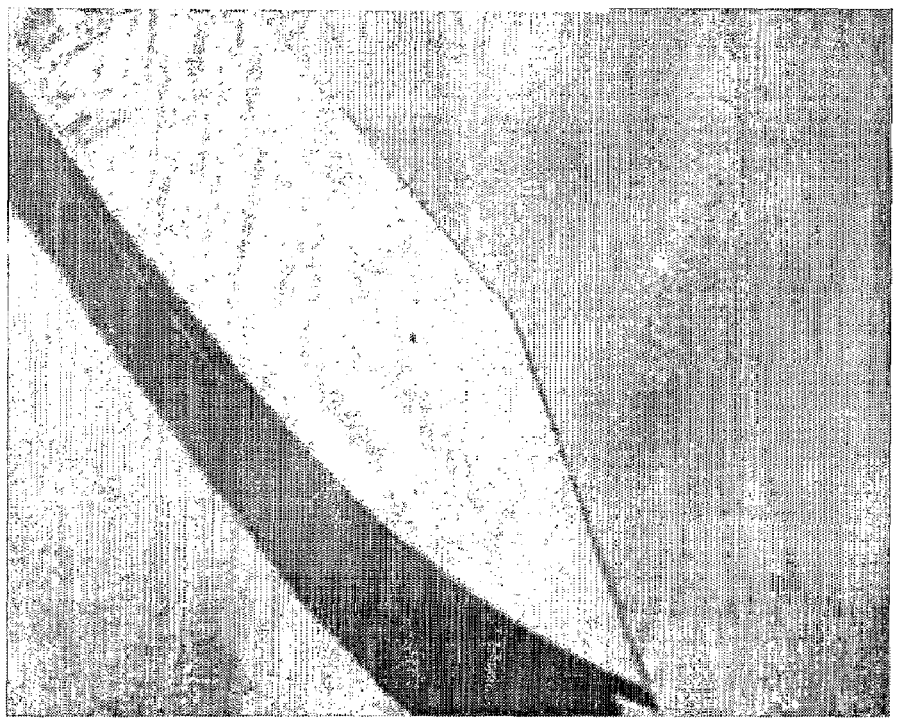

FIGS. 2-4 illustrate the fingerprint detection and lifting capabilities of the invention applied to three common items and surfaces that often bear fingerprints: A hard cover book (FIG. 2), a plastic CD case (FIG. 3), and a stainless steel Swiss army knife (FIG. 4). The images of FIGS. 2A, 3A and 4A illustrate a patch on the book cover, the CD case, and the knife, respectively, under ordinary lighting, i.e. a lighting setup different from the special configuration determined by the method of the invention as described below. The images of FIGS. 2B, 3B and 4B are processed results from image sets taken under the specially arranged lighting configuration of the invention. As illustrated, in each case the visibility of the fingerprint mark is significantly enhanced. The images of FIGS. 2C, 3C and 4C are the results obtained from the same image sets as in FIGS. 2B, 3B and 4B, respectively, but processed differently to extract a different polarization related physical quantity. As illustrated, the technique of the invention selectively enhances only the real fingerprint and at the same time suppresses irrelevant background patterns to yield a clean "fingerprint-only" image.

FIG. 5 illustrates a step-by-step application of the optical method of the invention for non-contact detection and extraction using the arrangement of FIG. 1(D) for imaging a latent fingerprint on a metal case. In the case of the images of FIG. 5, the "specular" lighting condition is formed by incandescent light source 10 behind a diffuser (not shown), and the camera 20 is adjusted close to the angle of specular reflection from the surface 30. FIGS. 5(A) and 5(B) illustrate images taken with ordinary room lighting: the contrast of the fingerprint is so low that the mark is not visible, even when a highly sensitive CCD camera 20 and digital contrast enhancements are used. In the image of FIG. 5(A), the recorded intensities were linearly rescaled to utilize the full 8-bit dynamic range of the display 60 (the brightest pixels in the image were set to the maximum possible value allowed by the display 60 and the darkest pixels to the lowest display value and the rest of the pixel intensity values were linearly rescaled), while in the image of FIG. 5(B) histogram equalization contrast enhancement was instead applied. This latter contrast enhancement method remaps the pixel values according to the histogram distribution of their magnitudes, distributing them more evenly over the dynamic range of the display. The images of FIGS. 5(C) and 5(D) were taken with the same setup as in FIGS. 5(A) and 5(B), but now specially arranged lighting producing specular reflection over the surface 30 of the metal case has been employed and the ordinary room light has been turned off. The camera 20 was orientated relative to the light source 10 and surface 30 so that predominantly the specular component of reflection from the surface 30 was recorded. FIG. 5(C) employs a linear resealing contrast enhancement and FIG. 5(D) histogram equalization. FIG. 5(E) presents a cropped and enlarged version of the image of FIG. 5(C) to show the details of the fingerprint. FIG. 5(F) is a further cropped and enlarged version of the image of FIG. 5(E) to reveal the high quality of recovered fingerprint mark. The quality of this image exceeds that of many exemplar fingerprint images. FIG. 5(G) shows the image in FIG. 5(E) reprojected to upright canonical orientation for database/archiving purposes.

Figure 5A:
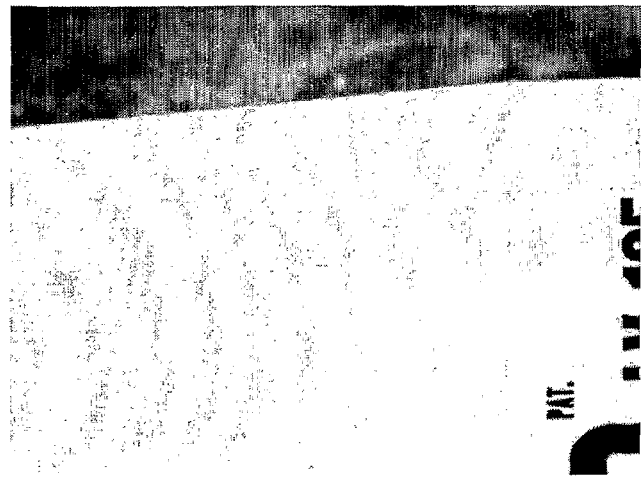
FIGS. 5(A)-5(G) illustrate a step-by-step application of the optical method of the invention for non-contact detection and extraction using the arrangement of FIG. 1(D) for imaging a latent fingerprint on a metal case.
Figure 5B:
Figure 5C:
Figure 5D:
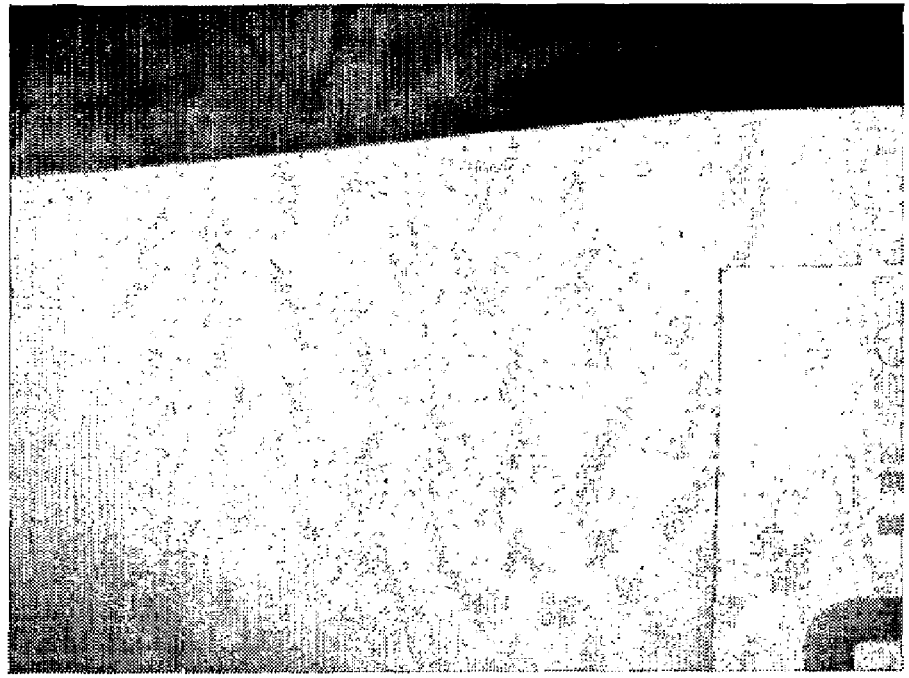
Figure 5E:
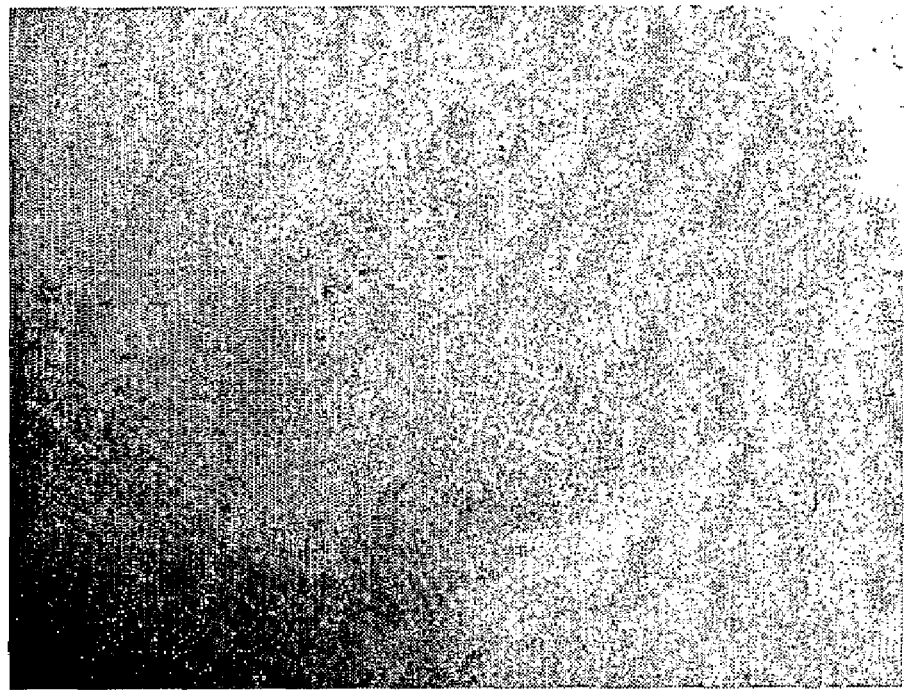
Figure 5F:
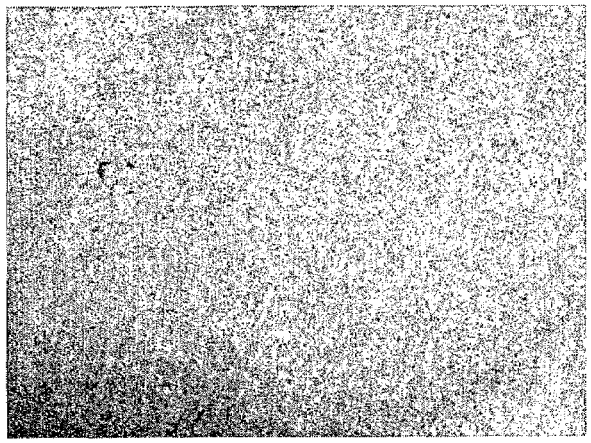
Figure 5G:
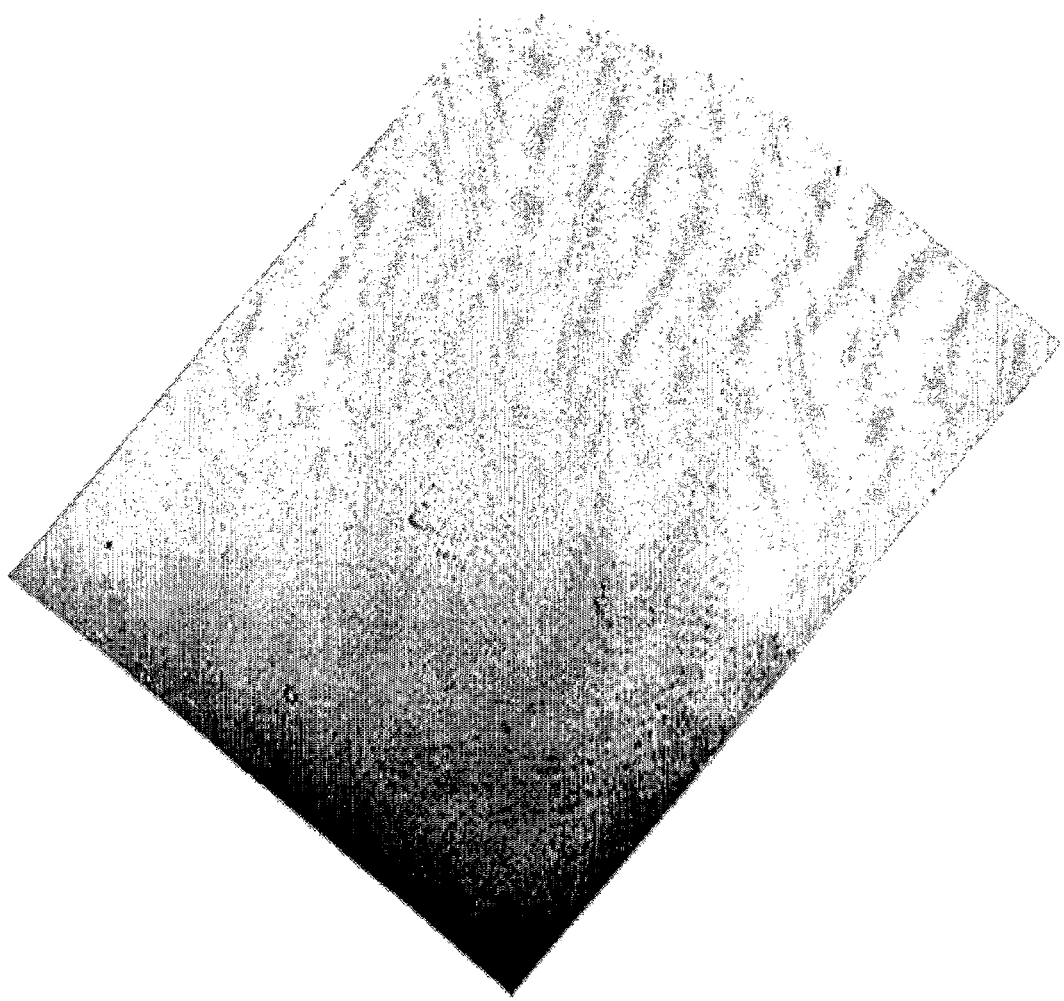

The images of FIGS. 5(A) and 5(B) illustrate the 'latent' nature of the fingerprint: the natural contrast is so low that not only the unaided human eye cannot detect it, but even widely used digital image enhancements do not reveal its presence. FIGS. 5(C) and 5(D) illustrate that imaging the light specularly reflected from the surface 30 yields a major enhancement not achievable with the digital enhancements alone, an enhancement traditionally achieved with powders and chemicals, but completely without destructive side effects. It will be appreciated by those skilled in the art that many existing contact technologies, if applied to the same fingerprint sample, would produce images with less quality than the method of the invention. For example, the powder dusting method may have powder adhering to the residue non-uniformly and create additional artifacts in the lifted fingerprint pattern.

Figure 6A:
FIGS. 6(A)-6(C) illustrate the use of polarization information in accordance with the optical method of the invention to extract a fingerprint from the paper cover of a desk calendar with an underlying picture pattern (picture of several jet fighters in formation).
Figure 6B:
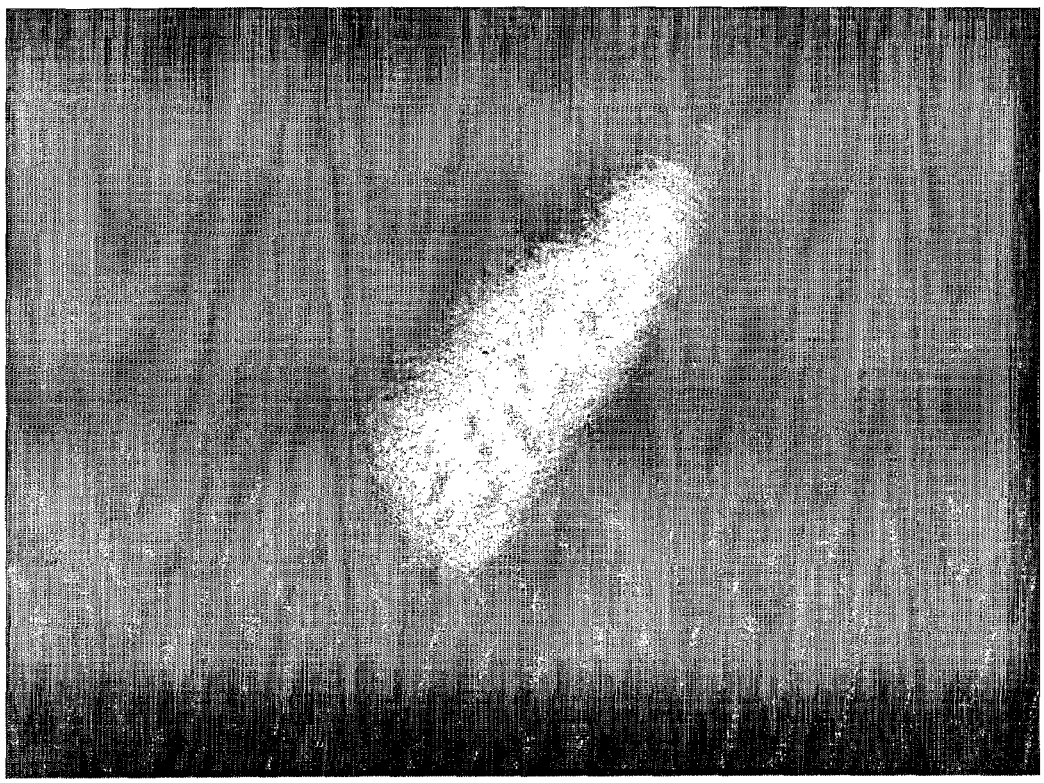
Figure 6C:
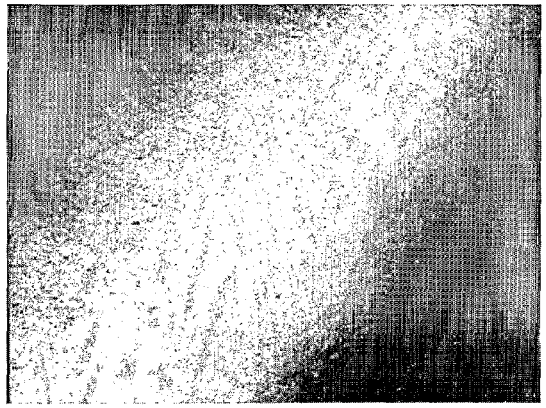

FIG. 6 illustrates a further enhancement of non-invasive optical latent fingerprint extraction achieved by using polarization information in accordance with the invention. In FIG. 6, the surface 30 inspected is the paper cover of a desk calendar with an underlying picture pattern (picture of several jet fighters in formation). FIG. 6(A) illustrates the result obtained without using a polarization filter 40, and only with specular lighting. FIG. 6(B) illustrates the distribution of the physical quantity $I_A$ as given by Equation 6 below. This quantity is computed from at least three images of the same scene taken with a linear polarization analyzer set at three different angles (e.g., 0°, 45°, and 90°). Of course, other polarization angles may also be used so long as they are dissimilar enough to extract information that are all different from each other (i.e., not parallel or anti-parallel). At least three images are taken so that the three variables of Equation 6 may be resolved by a conventional computing apparatus. In other words, at least three different images of the same scene with different polarizations for each image are detected and the resulting images are processed to solve for the variables in Equation 6 for every pixel, namely, total pixel intensity ($2I_U$), degree of linear polarization the polarized intensity (or polarization difference intensity) $I_A$ (p), and the orientation angle of the major axis of the polarization ellipse (θ). FIG. 6(C) illustrates a cropped view of the image of FIG. 6(B) to show the details of the fingerprint pattern recovered. All images in FIG. 6 were digitally enhanced with the histogram equalization technique.

The paper cover of an ordinary desk calendar imaged in FIG. 6 presents a greater challenge than the metallic surface imaged in FIG. 5. The paper surface contains a printed pattern whose light absorption interferes with the optical detection of the fingerprint. Thus, both specular reflection and polarization analysis are used to extract the latent fingerprint in FIG. 6(B). For the polarization analysis, images are taken with a linear polarization analyzer mounted in front of the camera 20, and oriented at three different angles. Those skilled in the art will appreciate that the arrangement may include one rotating linear polarization analyzer that changes the direction of the polarized filters 40 in front of the camera 20 for each measurement; on the other hand, several independent polarization filters 40 and/or multiple cameras 20 may be used to obtain the differently polarized images. FIG. 6(B) is not an image of the ordinary intensity distribution, but rather a mapping of a certain physical quantity derived from the polarization distribution of the light comprising the image. The specular component of the surface reflection is now evident, and the background pattern is gone. These results lead to two conclusions: first, the non-invasive optical method can extract latent prints from some paper surfaces as well as from smoother surfaces; and second, the processing of the polarization information in the image can further enhance the quality of the recovered latent fingerprint under certain conditions.

Figure 7A:
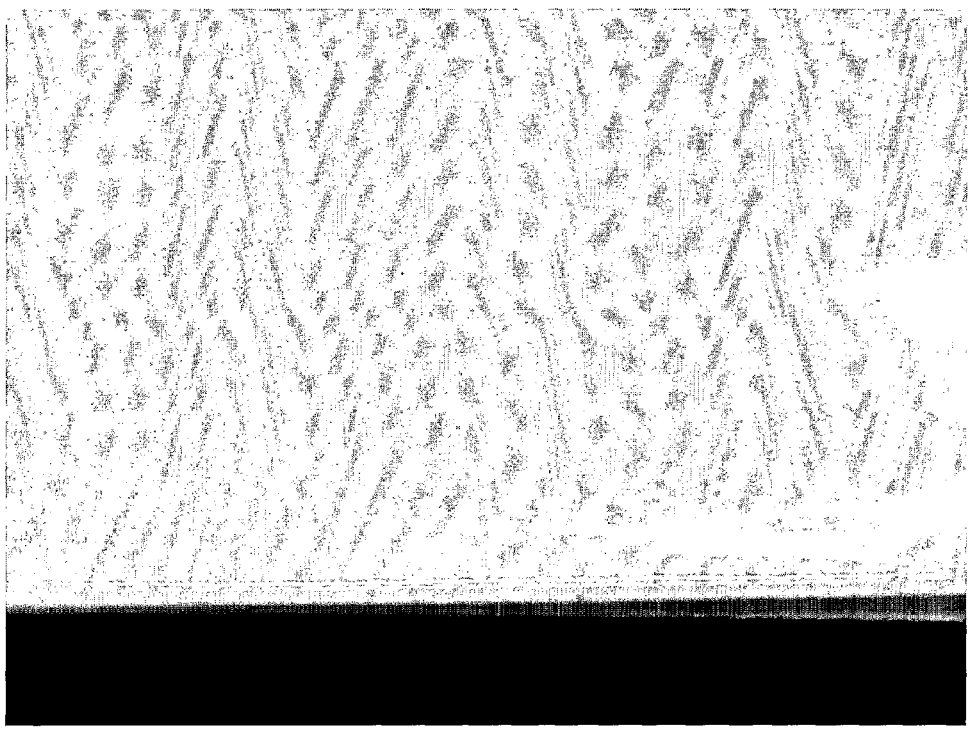
FIGS. 7(A)-7(D) illustrate the use of the optical method of the invention to extract a fingerprint from a soft clear plastic CD sleeve having a white cotton lining underneath which obscures the specular reflection component with a more intense diffuse reflection.
Figure 7B:
Figure 7C:
Figure 7D:

In some objects on which latent fingerprints are left, the specular reflection component can be obscured by a more intense diffuse reflection. The optical methods and arrangement of FIG. 1(D) of the invention were applied to such a case, deliberately picking one of the strongest diffuse reflectors, a white cotton lining underneath a soft clear plastic CD sleeve. White surfaces have the highest diffuse reflection coefficients and can sometimes overwhelm specular reflection signals. FIG. 7(A) illustrates an image taken without a polarizing filter 40 in front of the camera 20. As illustrated, the diffuse white light is so strong that the specular reflection output can barely enhance the latent fingerprint on the plastic surface. FIG. 7(B) illustrates the distribution of the quantity $I_A$ from Equation 6 below, revealing polarization information in the reflected light. The latent fingerprint now pops out with a very high contrast. FIG. 7(C) illustrates a close-up view of the fingerprint area in FIG. 7(B), while FIG. 7(D) illustrates the reprojected canonical image of FIG. 7(C) for database/archiving purposes. All images in FIG. 7 were enhanced with histogram equalization and, as illustrated in FIGS. 7(B) and 7(C), the polarization-based analysis followed by the histogram equalization readily enhanced the latent fingerprint.

Materials and Methods

The experimental setup used in FIG. 1(D) to generate the images of FIGS. 2-7 includes a digital Single Lens Reflex (SLR) camera 20 (Olympus E-10) with a built-in 9 mm-36 mm focal length zoom lens (permanently attached, not changeable), a matching macro extension lens pro (Olympus MCON-35), a matching 72 mm (diameter) linear polarizer 40 (TAMRON (FPL72)), and a remote cable RM-CB1 (Olympus). The light source 10 can be any ordinary house light. The one used to obtain the images was a 150 W incandescent bulb (Philips DuraMax) and a small 13 W fluorescent light (Philips ECOTONE PL-S 827/2P). Although it can be shown that a point light source may be assumed (or a source at a large distance from the object), in practice better results were obtained by placing an opal glass diffuser in front of a light bulb. Those skilled in the art will appreciate that because specular reflection is mirror-like, a bulb without a diffuser will cause its own image pattern to show up in the specular reflection, whose occurrence may interfere with the fingerprint pattern to be extracted. A diffuser acts as a spatial low-pass filter, removing the high spatial frequency pattern of the shape of the light source 10 itself. Due to the geometry, the majority of the light energy that actually reaches the surface 30 under examination is relatively uniform, in conformance to basic assumptions. This greatly facilitates the digital image processing to be performed. The CCD (charge-coupled device) chip in the Olympus E-10 SLR camera 20 has a ⅔ inch format with dimensions 6.6 mm in height and 8.8 mm in width. A picture captured by the camera 20 contains 2240× 1680 pixels (the actual number of recorded pixels is 2256× 1684). The digitizer can distinguish 10 bits ($2^{10}$=1024) of different gray levels. The camera 20 saves images in the flash memory in either JPEG (Joint-Photographic Experts Group) format, TIFF (Tagged Image File Format), or RAW. It is important to note that in order to perform accurate pixel-by-pixel computations, the images illustrated in FIGS. 2-7 were saved in the RAW format. The images saved in TIFF format are not compressed but would be modified by a built-in processing algorithm of the digital camera 20 before saving in order to provide better looking images. The JPEG format further distorts the pixel values by introducing lossy compression to save the storage space. Only the RAW format precisely records the raw read-out values directly from the digitization output of the CCD that is suitable for the computations set forth herein. The RAW format is also the only format that records the full 10-bit intensity data from the CCD output; all other formats record only standard 8-bit data. The added 2 bits yields 4 times more distinguishable image gray levels that can significantly enhance the results of digital calculations needed for polarization analysis as set forth below.

Surface Reflection Calculations

By understanding the underlying optical and mathematical basis of the invention, those skilled in the art will appreciate that the methods of the invention may be used to extract fingerprints of a wide variety of surfaces with a wide variety of optical characteristics. Those skilled in the art will also appreciate that the model of the surface reflection in a microscopic scale is complicated and depends heavily on the detailed knowledge of the molecular material composition of the surface material. However, macroscopically, a more general model can be used that applies to a wider range of surfaces 30 without the need for details about the surface 30 with acceptable reduction in accuracy. This is desirable in many practical applications, notably in computer vision and graphics, where the details of the chemical and physical composition of surfaces 30 are not known or are not of vital importance. Many surface reflection models are based not on the exact chemical composition but rather on a plausible statistical model of the surfaces 30. Because it is the inventors' intentions to extract the fingerprint without using any chemical analysis, the possibility of knowing the properties of surface material beforehand is excluded. However, a simple model that describes a general trend is good enough, because the ultimate form required for a fingerprint image is that of binarized black and white regions separating the ridge and furrow areas of the finger. There is no need to recover or to predict the exact brightness differences in the gray-level images taken for the purpose of recovering fingerprint marks. The simple Phong model and Lambertian model, both widely used in many computer vision and graphics algorithms, satisfy these purposes.

Macroscopically, two general types of reflection can be named. The Lambertian model describes a surface 30 producing perfectly diffuse reflection as:

$$I = I_p k_d \cos\theta = I_p k_d (\hat{n} \cdot \hat{l}) \qquad (1)$$

where I is the intensity of the image point sensed by the camera 20, $I_p$ is the point light source's intensity, $k_d$ is the reflection coefficient (either for a particular wavelength or for a particular camera's spectral response), and θ is the angle between the surface normal n̂ and the unit vector l̂ in the direction of the light source 10 as viewed from the point of reflection. Note that the diffuse reflection has the same intensity for all viewing directions.

Another type of reflection is that of highlights, or mirror like reflection observed on many smooth surfaces. A more subdued version is usually called "sheen". The Phong model is given by:

$$I_\lambda = I_{a\lambda} k_a O_{d\lambda} + f_{att} I_{p\lambda} [k_d O_{d\lambda} \cos\theta + W(\theta) \cos^n \alpha] \qquad (2)$$

where λ is the wavelength of the light, subscript 'a' denotes ambient light source, subscript 'p' denotes point light source, subscript 'd' denotes a diffuse reflection component, the new symbol O denotes color components in human and digital color vision components, $f_{att}$ is the inverse square of decay distance of a point light source intensity, W(θ) is the diffuse reflection coefficient of the surface 30 with a point light source angle of incidence θ, α is the angle between the exact view direction predicted by the law of reflection and the actual view direction, as shown in FIG. 1(D). For the present invention, the most important information derived from Equation (2) is that the intensity depends on α as $\cos^n \alpha$. This gives a simple way to model a rapid decay in intensity if the view angle is different from that predicted by the law of reflection. This term suggests that if the camera 20, the light source 10, and the surface 30 being inspected are arranged in a way predicted by the reflection law (FIG. 1(D)), the image point for the original smooth surface 30 without skin residue will show intensity typical for specular reflection, while the area with skin residue will have much less specular reflection due to the slight change in the direction of surface normal caused by the skin residue. The more mirror like a surface 30 can be modeled, the larger power of cosine decay it exhibits, which means better contrast in the specular-reflection—based latent fingerprint detection and lifting technique of the invention.

Provided that all other factors are equal, the intensity of the specular reflection component is in general much stronger than the diffuse reflection component. Although, this statement is not always true, it has been widely accepted as a good rule of thumb in the majority of practical situations. Since the specular reflection has a tendency of concentrating reflected energy in a small solid angle, as opposed to the diffuse reflection which spreads all the reflected energy into a full hemisphere, the same amount of reflected energy will result in a much greater flux density in specular reflection and thus the image brightness. The specular reflection tends to be reflected only once from the smooth surface 30, while the diffuse reflection gives light that experienced a multiple scattering inside the surface 30 before re-emerging. Each scattering only weakens the intensity but seldom enhances it. As reported in *Image and Visual Computing*, Vol. 13, page 497 (1995), Wolff et al. experimentally measured the ratio between specular and diffused reflection intensities for several different surfaces and reported ratios varying from about 150:1 to 250:1. For many digital sensors with 8-bit brightness resolution, this is close to the maximum intensity ratio of 255:1. This gives a strong support to the main assumption, namely that the specular reflection component is in general stronger than the diffuse one.

Wolff also reported another important theoretical result relating to fingerprint detection, namely, if the reflection coefficient of the diffuse component is about ⅓₃ more than the reflection coefficient of the specular component, then the diffuse component can be stronger or at least comparable to the specular component. If the underlying surface consists of complicated patterns similar in strength and spatial frequency to the latent fingerprint pattern on top of it, the method based on a purely specular reflection is not satisfactory. This is the point where a polarizer 40 should be used.

The behavior of specular component is governed by the well-known Fresnel reflection coefficients formula:

$$r_\perp \equiv \left(\frac{E_{0r}}{E_{0i}}\right)_\perp = \frac{n_i \cos\theta_i - n_t \cos\theta_t}{n_i \cos\theta_i + n_t \cos\theta_t} = \frac{\sin(\theta_i - \theta_t)}{\sin(\theta_i + \theta_t)} \quad (3)$$

$$r_P \equiv \left(\frac{E_{0r}}{E_{0i}}\right)_P = \frac{n_t \cos\theta_i - n_i \cos\theta_t}{n_t \cos\theta_i + n_i \cos\theta_t} = \frac{\tan(\theta_i - \theta_t)}{\tan(\theta_i + \theta_t)}$$

where subscripts 'i', 't', and 'r' stand for incident, transmitted, and reflected component. The subscripts '⊥', and '∥' are related to the plane of incidence. In FIG. 1(B) the plane of this paper is the plane of incidence. In the case of specular reflection, it contains both the incident and reflected light wave vectors. It is well known that $r_P$ can be exactly zero at the Brewster's angle $\theta_B$, which is given as:

$$\tan\theta_B = \frac{n_t}{n_i}. \quad (4)$$

If light is incident from the air, $n_i \approx 1$, while $n_t$ varies from 1.4 to 2.0 for most dielectrics in the visible band (wavelength of about 400~700 nm). Equation (4) shows that the corresponding Brewster's angles vary from 55 to 74 degrees, respectively. Although, there are certain materials with higher refractive index, the discussion herein will be confined to the above-mentioned range of $n_t$. Therefore, when an angle of incidence between 55 and 74 degrees is considered, the reflected light is highly partially polarized with the plane of polarization perpendicular to the plane of incidence. This case is referred to as "horizontal polarization" with respect to the surface 30 being inspected. Dielectric surfaces which are adequate in most cases are discussed herein since "pure" metallic surfaces are rather rare in everyday life. Pure metal surfaces are oxidized quickly and the actual layer "responsible" for specular reflection is often either the oxides on the surface 30 or the protective painting layer which is also a dielectric material. In fact, many metallic-looking merchandise today is actually coated with highly reflective dielectric paints. In cases when the underlying pure metal reflects more light than the upper dielectric coating, the method of the invention may not work on such a surface.

The general expression for observed intensity of partially polarized light I as a function of the angle of orientation of a polarization analyzer φ can be written as follows:

$$I(\phi) = I_U + I_A \cos[2(\theta-\phi)] = I_U\{1 + p\cos[2(\theta-\phi)]\}, \quad (5)$$

where θ is the orientation angle of the major axis of the polarization ellipse, $I_U$ is a half of the total pixel intensity, and $p \equiv I_A/I_U$ is the degree of linear polarization at the pixel. The reference axis for φ and θ can be arbitrarily chosen. Since the exact index of refraction of the surface 30 having the latent fingerprint is considered unknown, putting one polarizer 40 at a given orientation angle in front of the camera 20 and taking a picture can not provide the complete information about the polarization state of the received light. However, by taking three pictures with the polarizer 40 oriented at three different angles, for example φ=0, 45 and 90 degrees, one can recover $I_U$, $I_A$, and θ for each pixel of the image using the following expressions:

$$I_U = (I_0 + I_{90})/2$$

$$I_A = \sqrt{(I_{45} - I_U)^2 + (I_{90} - I_U)^2}$$

$$\theta = \arctan[(I_{45} - I_U)/(I_{90} - I_U)]/2 \quad (6)$$

Here, indices 0, 45, and 90 indicate the orientation of the polarizer 40 in degrees when the image was taken. Because θ and θ+π are indistinguishable for phase-blind visual sensors in most conventional cameras, the meaningful range of θ is restricted by π (i.e., θ usually ranges from 0 to π). A system of two cameras with a controllable polarizer 40 and a beam splitter to rapidly take the required pictures may be implemented to acquire the polarized images. Of course, different polarization indices may also be used.

Since the background object pattern is most likely caused by pigments beneath the transparent substrate that is used to hold them, the object pattern intensity signals are mostly due to diffuse reflection, which is nearly unpolarized and thus $I_A$ and sometimes p are almost zero. Thus, with the polarization technique of the invention, one can extract the purely specular reflection component from the top surface 30 by computing images of $I_A$ or p for every image point. Such images often carry a substantial contrast between the fingerprint residue pattern and the clean area in between.

ADVANTAGES OF THE INVENTION

The non-contact, optical method for detecting latent fingerprints in accordance with the invention has several advantages over existing methods. First, the method is inherently non-invasive, and thus may recover latent fingerprints without damaging or altering the object bearing the fingerprints, nor altering the latent prints themselves. Preservation of the latent print in its original form can be very useful, since application of any method can fail and one may need to apply several different methods. It has also been reported from the experience of well-known crime labs that applying more than one latent fingerprint detection technique on the same surface may well reveal very different fingerprints for each technique. Also, the lifting of a powdered print can fail, with only part of the powder and the residue being lifted. It is a standard precautionary procedure to photograph the fingerprint before attempting to lift it with sticky tapes. Preservation of the object on which the latent print resides is highly desirable, as valuable objects, particularly those that cannot be ever replaced, may be seriously damaged by the chemical treatments commonly used to lift fingerprints. For example, the iodine fume is known to be highly corrosive and toxic, while treatment with ninhydrin and DFO require the object being soaked with chemical solution followed by being baked to close to or over 100 degrees Celsius. Clearly there are many fingerprint bearing objects that would not survive the harsh treatments by chemicals and high temperature.

Second, by not using any chemicals the method of the invention does not need to wait for slow chemical reactions to develop the enhanced fingerprint marks. The digital imaging and processing only take up to a few minutes. In contrast, certain chemical fuming can take hours or even days before a usable fingerprint mark is developed.

In addition, the equipment needed to implement the method of recovering latent fingerprints in accordance with the invention is cost-effective and commonly available. All that is required in the simplest cases is a digital camera 20 with a sufficient dynamic range (intensity depth) and a reasonable resolution (pixel density). A camera is needed in any case with traditional powdering or chemical methods to document fingerprint evidence, and likewise as a backup for other invasive latent fingerprint recovering methods. With the polarizing filter 40 (a common accessory for cameras) mounted on the camera 20, the capabilities of the method can be greatly expanded, as demonstrated in the examples above. Most other non-contact optical methods of which the inventors are aware—laser-induced luminescence and RUVIS—require a specialized high power laser or ultraviolet laser light source which are much more expensive and the high power laser is also non-portable. The episcopic coaxial illumination method is a much more limited method that does not have the benefit of adjusting the angles of lighting and viewing and without the use of polarization information. In contrast, the lighting requirements for the method of the invention can be met with any regular light source. For more difficult cases in which latent prints are obscured by diffuse reflection, a polarizer 40 is also required to further enhance the contrast of the fingerprint pattern from a strongly diffuse background. A digital computer will also greatly help in the computation of the polarization parameters and some basic digital contrast enhancement and reprojection, though in principle the calculation can also be done in other ways. However, the addition of a digital computer is generally not a problem, as those skilled in the art will appreciated that commonly available desktop and laptop computers today have sufficient power to import and process digital images with reasonable speed.

Of course, the non-contact optical method of the invention does have limitations, like any existing method. It works best on relatively non-porous, non-absorbent, smooth and flat surfaces. Latent prints on gently curved surfaces can still be recovered, but several pictures may be required in order to get all parts of the latent fingerprint, and additional processing may be needed to render the print into a standard, flattened projection.

Those skilled in the art will also appreciate that the invention may be applied to other applications besides fingerprinting without departing from the scope of the invention. For example, the techniques of the invention may be used to detect minute deformations in the surfaces of structures, including hairline fractures, warping, shifting, or cracking of high precision devices, airplane structures, and the like. Subtle brush strokes left by painters painting a wall have been found to be greatly enhanced and clearly visible with a variation of polarization imaging technique introduced in this invention. Shoe prints left on a pliable dielectric surface are also good candidate for enhancement and detection using the techniques and apparatus of the invention. The techniques of the invention may also be used to detect stress and/or strain that cause minute changes in the microstructure of a high precision device. Accordingly, the scope of the invention is not intended to be limited to the exemplary embodiment described above, but only by the appended claims.

What is claimed:

1. A method of generating an image of a deformation of a surface, comprising:
    applying light to said surface at a position to be examined for said deformation, said light having an angle of incidence with said surface in such a way that the specularly reflected component of the light from the light source by the surface or by the deformation will be captured by an observing camera;
    receiving light reflected by said surface and/or by a deformation on said surface in said observing camera after said light at said angle of incidence has interacted with said surface and said deformation;
    generating at least two images of said reflected light received by said camera from the surface and/or the deformation;
    processing said at least two images to extract first and second polarization parameters; and
    displaying an image of said deformation, where the image pixel values represent the contours of the deformation on the surface at said position and comprise said first and/or said second polarization parameters of said reflected light from said surface at said position.

2. A method as in claim 1 wherein the deformation is a latent fingerprint, further comprising:
    filtering the reflected light from said surface with a polarizing filter whereby respective generated images represent images captured with the polarizing filter oriented in different directions;

said processing said at least two images comprises calculating angle of polarization, degree of linear polarization, and/or polarization light intensity as said first and second polarization parameters; and said displaying comprises displaying an image of at least one of the first and second polarization parameters, each pixel of said image comprising at least one of the computed polarization parameters of said reflected light from said surface at said position.

3. A method as in claim 2, wherein said filtering comprises moving different polarization filters to a filter position between said surface and said observing camera for reception of said reflected light by said observing camera.

4. A method as in claim 3, wherein said step of generating at least two images comprises the steps of generating at least three images of said surface at said position with respective polarization filters having angles of 0°, 450° and 90°.

5. A method as in claim 2, wherein said processing includes the step of processing said images to improve intensity contrast and/or polarization contrast between a portion of the image containing said surface and a portion of the image containing said latent fingerprint.

6. A method as in claim 2, wherein said processing includes the step of calculating said polarization parameters for each pixel in the image.

7. A method as in claim 2, wherein said displaying step comprises the step of selectively displaying calculated light intensity information at each pixel of said image, calculated light polarization information at each pixel of said image, and a combination image where each pixel comprises a function of said calculated light intensity information and said calculated light polarization information.

8. A method as in claim 7, further comprising the step of selecting for display the image providing the best contrast between the surface and the latent fingerprint.

9. A system for generating an image of a deformation of a surface without touching the surface, comprising:

a light source oriented so as to apply light to said surface at a position to be examined for said deformation, said light having an angle of incidence with said surface;

a camera oriented so as to receive light reflected from said surface and/or by a deformation on said surface after said light at said angle of incidence has interacted with said surface and said deformation; and a processor that generates at least two images of said reflected light received by said camera from the surface and/or from the deformation, processes said at least two images to extract first and second polarization parameters, and generates an image of said deformation, where the image pixel values represent the contours of the deformation on the surface at said position and comprise said first and/or said second polarization parameters of said reflected light from said surface at said position.

10. A system as in claim 9, further comprising a polarization filter that can be oriented with at least two different orientations that are respectively disposed between said surface and said camera when respective images of said at least two images are generated.

11. A system as in claim 10, wherein different polarization filters have angles of 0°, 45° and 90° and said camera generates three images, one with each respective filter disposed between the camera and the surface.

12. A system as in claim 9, wherein said processor further processes said images to improve intensity contrast and/or polarization contrast between a portion of the image containing said surface and a portion of the image containing said deformation.

13. A system as in claim 9, wherein said processor calculates said at least two polarization parameters for each pixel in the image.

14. A system as in claim 9, wherein said processor presents to a display for selection by a user calculated light intensity information at each pixel of said image, calculated light polarization information at each pixel of said image, and a combination image where each pixel comprises a function of said calculated light intensity information and said calculated light polarization information.

15. A system as in claim 14, wherein said processor displays one of said light intensity image, said light polarization image, and said combination image automatically based on reflection characteristics of said surface.

16. A system as in claim 9, wherein said light source is one of an incandescent and a fluorescent light source.

17. A system as in claim 9, wherein said camera is disposed in such a way such that a substantial portion of the specular reflection of said light off of said deformation is not captured.

* * * * *

UNITED STATES PATENT AND TRADEMARK OFFICE
CERTIFICATE OF CORRECTION

PATENT NO.        : 7,489,391 B2                                        Page 1 of 1
APPLICATION NO.   : 11/587349
DATED             : February 10, 2009
INVENTOR(S)       : Nader Engheta et al.

It is certified that error appears in the above-identified patent and that said Letters Patent is hereby corrected as shown below:

Column 2,
Line 24, delete "two" and insert -- few --.

Column 10,
Line 60, delete "not" and insert -- *not* --.

Column 12,
Line 48, delete "I" and insert -- *I* --.
Line 52, delete "î" and insert -- *î* --.

Signed and Sealed this

Twenty-seventh Day of April, 2010

David J. Kappos
*Director of the United States Patent and Trademark Office*